US012784319B2

(12) United States Patent
Osthus et al.

(10) Patent No.: US 12,784,319 B2
(45) Date of Patent: Nov. 3, 2026

(54) VIRTUAL AVATAR GENERATION AND SIMULATION FOR SELF-IMPROVEMENT APPLICATIONS

(71) Applicant: LEAP ROAD, INC., Miami, FL (US)

(72) Inventors: Torsten Osthus, Roetgen (DE); Deepak Gopalakrishnan, Kerala (IN)

(73) Assignee: Leap Road, Inc., Miami, FL (US)

( * ) Notice: Subject to any disclaimer, the term of this patent is extended or adjusted under 35 U.S.C. 154(b) by 112 days.

(21) Appl. No.: 18/827,700

(22) Filed: Sep. 7, 2024

(65) Prior Publication Data

US 2026/0073604 A1 Mar. 12, 2026

(51) Int. Cl.

| | |
|---|---|
| ***G06T 13/40*** | (2011.01) |
| ***G06F 40/40*** | (2020.01) |
| ***G16H 10/20*** | (2018.01) |
| ***G16H 20/70*** | (2018.01) |

(52) U.S. Cl.

CPC .............. *G06T 13/40* (2013.01); *G06F 40/40* (2020.01); *G16H 10/20* (2018.01); *G16H 20/70* (2018.01)

(58) Field of Classification Search

CPC ......... G06T 13/40; G06F 40/40; G16H 10/20; G16H 20/70

See application file for complete search history.

(56) References Cited

U.S. PATENT DOCUMENTS

| | | | | |
|---|---|---|---|---|
| 10,878,817 | B2 * | 12/2020 | Toplyn | G06F 40/40 |
| 11,380,039 | B2 * | 7/2022 | Miller, IV | G06F 17/18 |
| 11,423,886 | B2 * | 8/2022 | Gruber | B60K 35/00 |
| 12,272,265 | B2 * | 4/2025 | Naufel | G06F 40/40 |
| 2001/0019330 | A1 | 9/2001 | Bigmore | |
| 2008/0221892 | A1 | 9/2008 | Nathan | |
| 2009/0216691 | A1 | 8/2009 | Borzestowski | |
| 2013/0257876 | A1 | 10/2013 | Davis | |

(Continued)

FOREIGN PATENT DOCUMENTS

| | | | | |
|---|---|---|---|---|
| EP | 4485478 A1 * | 1/2025 | | G16H 50/50 |

OTHER PUBLICATIONS

Peter R. Lewis, A Survey of Self-Awareness and Its Application in Computing Systems, Cercia workshop on Self-Awareness in Computing on Jun. 27, 2011.

*Primary Examiner* — Philip P. Dang
(74) *Attorney, Agent, or Firm* — CRGO Global; Steven M. Greenberg

(57) ABSTRACT

Virtual avatar generation and simulation includes registering an end user in a self-awareness computer program and establishing a communicative coupling to different heterogeneous data sources, so that characterizing data of the end user is received from over each coupling to each heterogeneous data source. The characterizing data is transformed into a knowledge graph associated with the end user and an avatar is instantiated in the self-awareness computer program in correspondence to the end user. Thereafter, an avatar generation prompt is formulated requesting parameterization of the avatar including both a reference to the knowledge graph and also a reference to the avatar. The prompt is then transmitted to a large language model (LLM) so as to receive in response the requested parameterization. Finally, the avatar is parameterized with the received parameterization and simulated in the self-awareness computer program with respect to a scenario artifact defining a scenario for the end user.

20 Claims, 3 Drawing Sheets

(56) References Cited

U.S. PATENT DOCUMENTS

| | | | | |
|---|---|---|---|---|
| 2022/0301250 | A1 | 9/2022 | Ko | |
| 2024/0029848 | A1* | 1/2024 | Gupta | G16H 15/00 |
| 2024/0104816 | A1* | 3/2024 | Shaw | G06T 13/40 |
| 2024/0220725 | A1* | 7/2024 | Gueret | G06F 40/30 |
| 2025/0005836 | A1* | 1/2025 | Chu | G06F 21/107 |
| 2025/0022200 | A1* | 1/2025 | Huang | G10L 13/047 |
| 2025/0131623 | A1* | 4/2025 | Boyd | G06T 11/00 |
| 2025/0181138 | A1* | 6/2025 | Schüller | G06T 13/40 |
| 2025/0181370 | A1* | 6/2025 | Klingler | G06F 9/453 |
| 2025/0181847 | A1* | 6/2025 | Schüller | G06F 40/35 |
| 2025/0182366 | A1* | 6/2025 | Klingler | G06T 13/40 |

* cited by examiner

VIRTUAL AVATAR GENERATION AND SIMULATION FOR SELF-IMPROVEMENT APPLICATIONS

BACKGROUND OF THE INVENTION

Field of the Invention

The present invention relates to the technical field of self-awareness data processing and more particularly to personality characterization for personal development data processing.

Description of the Related Art

Self-awareness, or mindfulness, is the "conscious knowledge of one's own character, feelings, motives, and desires, "according to the Oxford English Dictionary. More specific definitions include the ability of one to focus on himself or herself and how one's actions, thoughts, or emotions do or do not align with one's internal standards. Through self-awareness, one can objectively evaluate oneself, manage one's emotions, align one's behavior with corresponding values, and understand correctly how one is perceived by others. As can be seen, self-awareness, when achieved, can be of paramount importance to the ability of one to succeed in the personal and business interactions with others.

It is no surprise then that in the digitally connected world of today, many different self-awareness computer programs have been deployed for the purpose of helping individuals achieve self-awareness. The traditional self-awareness computer program ingests characterizing information regarding the end user, particularly demographic information, along with some stated goal or set of goals, for instance a type of job position, a health and wellness metric like weight or blood pressure, or an emotional outcome. The self-awareness program then processes the ingested data algorithmically in order to produce a provide different recommendations for physical or mental actions to be performed by the end user in order to drive towards the stated goal. As such, the ultimate use case for a given self-awareness computer program can range from personal growth and emotional well-being, to sales coaching, to job interviewing and career counseling.

An artificially intelligent bot has formed part and parcel of self-awareness computer program since the dawn of personal computing, harkening back to the venerable "Eliza" of Apple™ II fame. As one of skill in the art will recall, Eliza received textual input from an end user and based upon recognized language patterns within the textual input returned a pre-determined reply, in a conversational style. Advancements in artificial intelligence have evolved the bot paradigm in a self-awareness computer program context into a conversational agent visually represented by an avatar such that the concept of the bot and avatar merge into, simply a conversational avatar.

In some instances, the conversational avatar has been adapted to form the basis of human behavior prediction. Specifically, it has been known for many years to model the behavior of a human and then to simulate a scenario with the model in order to predict how the human would react to the scenario. Such arrangements have found particular application in competitive sport including video gaming. The key to a successful simulation using an artificially intelligent model of a human rests with the accurate definition of the model itself which requires substantial expertise at the time of the development of the model. And subsequent to the enormous consumption of resources in training such a model, the model remains static and does not adapt to the changing nature of the subject human.

BRIEF SUMMARY OF THE INVENTION

Embodiments of the present invention address technical deficiencies of the art in respect to self-awareness computing platforms and the use of an avatar to engage with an end user in a self-awareness computing platform. To that end, embodiments of the present invention provide for a novel and non-obvious method for virtual avatar generation and simulation. Embodiments of the present invention also provide for a novel and non-obvious computing device adapted to perform the foregoing method. Finally, embodiments of the present invention provide for a novel and non-obvious data processing system incorporating the foregoing device in order to perform the foregoing method.

In one embodiment of the invention, virtual avatar generation and simulation includes an initial registration of an end user in a self-awareness computer program and a subsequent establishment of a communicative coupling to multiple different heterogeneous data sources so that characterizing data of the end user may be received from over each coupling to each different heterogeneous data source. The characterizing data is then transformed into at least a portion of a knowledge graph in association with the end user. As well, an avatar may be instantiated in the self-awareness computer program in correspondence to the end user.

Once the avatar has been created, an avatar generation prompt may be formulated to request a parameterization of the avatar including both a reference to the knowledge graph and also a reference to the avatar. With the prompt formulated, the prompt may then be transmitted to a large language model (LLM) so as to receive in response to the prompt, the requested parameterization. Finally, the avatar is parameterized with the received parameterization. Consequently, the parameterized avatar can be simulated in the self-awareness computer program with respect to a scenario artifact defining a scenario for the end user.

Owing to the artificially intelligent parameterization of the avatar, the foregoing process of virtual avatar generation and simulation overcomes the deficiencies of the prior art in which an end user only interacts with a generic, static non-sentient entity programmatically responding to end user inputs in the self-awareness computer program. Specifically, in that the avatar is specifically tailored to the multi-source characterization of the end user, end user can be predicted based upon the simulation of a scenario by the avatar in place of the end user and then the end user can engage with the self-awareness computer program in a more natural way as a result of the familiar and emotionally compatible configuration of the avatar in order to understand the outcome of the scenario.

In one aspect of the embodiment, a performance of the parameterized avatar can be computed during the simulation. Then, the computed performance can be compared to a benchmark value. Finally, a threshold disparity can be recorded as between the computed performance and the benchmark value in the self-awareness program in connection with the end user.

Other aspects of the embodiment include variations of the characterizing data such as:

- The characterizing data includes answer data received from the end user in response to survey data presented to the end user in the self-awareness program.

The characterizing data includes data extracted from natural language processing of free form communications by the end user and captured in the self-awareness program.

The characterizing data includes demographic data extracted from a social media profile of the end user.

It is to be understood that any of the foregoing characterizations can be included as part of an aspect of the invention, alone or in varying combinations of one another.

In yet other aspects of the embodiment, during simulation the scenario artifact can be retrieved from a repository of artifacts each describing a different action to be taken by the end user. Thereafter, a predictive rule can be applied to the different action with at least a portion of the avatar as an input parameter to the predictive rule and a performance value can be received in response to the application of the rule.

Alternatively, an avatar simulation prompt to the LLM can be formulated which requests a performance value of the avatar in performing the action of the scenario artifact and which includes both a reference to the scenario artifact and also a reference to the avatar so that the prompt can be transmitted to the LLM and in response to which the requested performance value is received.

In another embodiment of the invention, a data processing system is adapted for virtual avatar generation and simulation. The system includes a host computing platform of one or more computers, each with memory and one or processing units including one or more processing cores. The system also includes a self-awareness computer program executing in the host computing platform. Finally, the system includes an avatar generation module. The module includes computer program instructions enabled while executing in the memory of at least one of the processing units of the host computing platform to perform virtual avatar generation and simulation.

In this regard, the program instructions perform the virtual avatar generation and simulation by registering an end user in the self-awareness computer program, establishing a communicative coupling to multiple different heterogeneous data sources and retrieving over each said coupling, characterizing data of the end user, transforming the characterizing data into at least a portion of a knowledge graph disposed in the memory and in association with the end user, instantiating an avatar in the self-awareness computer program in correspondence to the end user, formulating an avatar generation prompt requesting a parameterization the avatar and including both a reference to the knowledge graph and also a reference to the avatar, transmitting the formulated prompt to a large language model (LLM) and receiving the requested parameterization from the LLM in response to the transmitted avatar generation prompt, parameterizing the avatar with the received parameterization and directing the self-awareness program to simulate the parameterized avatar with respect to a scenario artifact defining a scenario for the end user.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for virtual avatar generation and simulation. In accordance with an embodiment of the invention, characterizing data of an end user registered with a self-awareness program can be collected from multiple different, heterogeneous data sources, such as traditional database tables of demographic data, ingested survey documents completed by the end user, and social media extracted data through an application programming interface (API) to different social media networks. The collected characterizing data is then transformed into a knowledge graph in association with the end user. Subsequently, an avatar for the self-awareness computer program can be instantiated according to a generic template subject to personalization for the end user through a parameterization of the instantiated avatar. To that end, an avatar generation prompt is formulated requesting the parameterization of the avatar and including both a reference to the knowledge graph and the prompt is submitted to an LLM in response to which the LLM returns the requested parameterization. The parameterization is then applied to the avatar in order to personalize the avatar in respect to the end user. Finally, the now personalized avatar can be simulated within the self-awareness computer program in respect to a scenario artifact defining a scenario for the end user.

Figure 1:
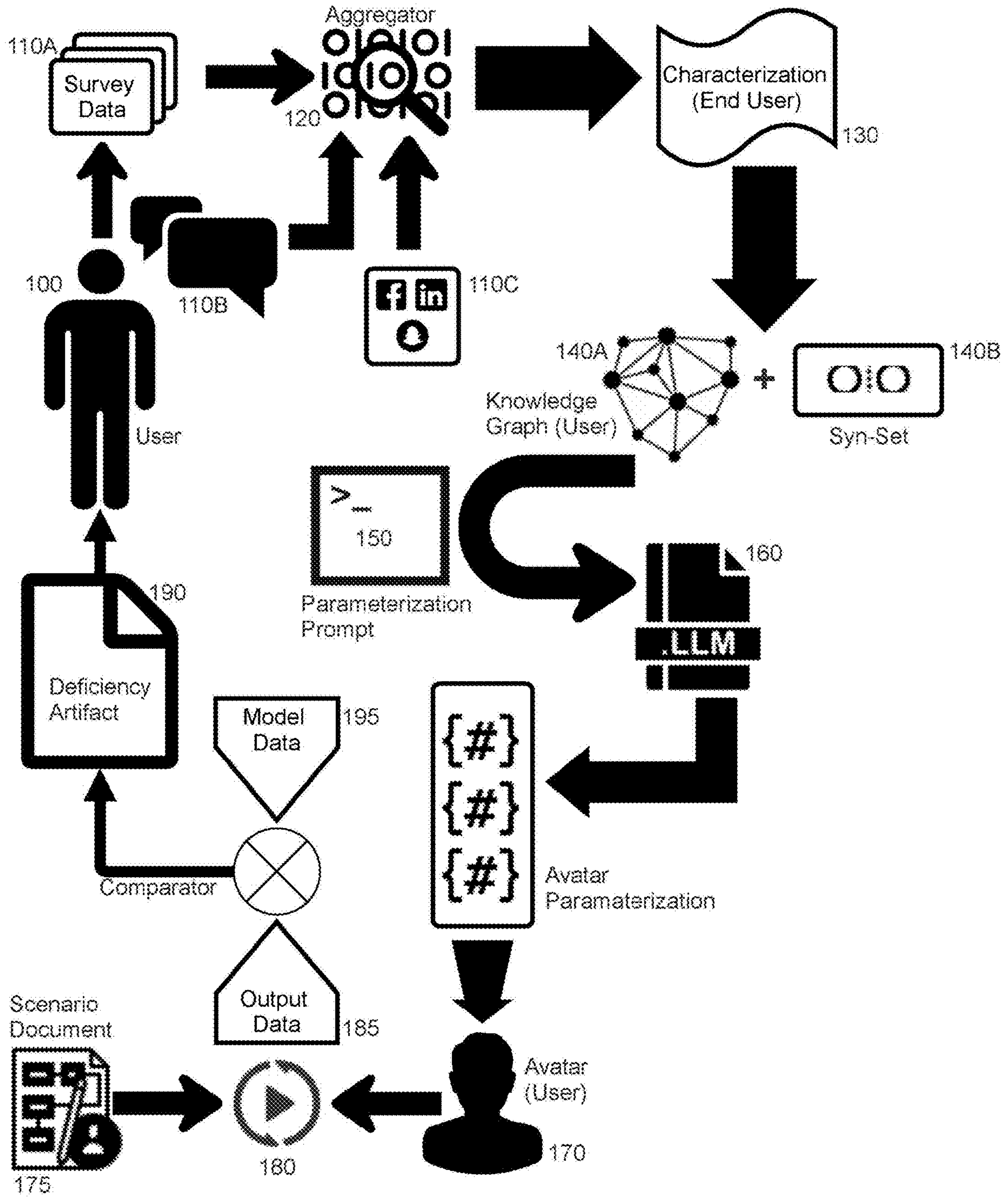
FIG. 1 is a pictorial illustration reflecting different aspects of a process of virtual avatar generation and simulation.

In illustration of one aspect of the embodiment, FIG. 1 pictorially shows a process of virtual avatar generation and simulation. As shown in FIG. 1, an end user 100 registers with a self-awareness computer program (not shown) and a data aggregator 120 collects characterization data 130 for the end user 100 characterizing personality traits and demographic traits of the end user 100. The characterization data 130 is collected at textual tokens of different phrases and sentences from a variety of heterogeneous sources including survey data 110A provided by the end user 100 in response to a survey questionnaire, real time answers 110B to an interactive question and answer session with the end user 100 and the aggregator 120, or as between the end user and an LLM (not shown) querying the LLM for a personality characterization of the end user 100, and social media network data 110C acquired by accessing social media postings and content associated with the end user 100.

Subsequently, an avatar 170 is created for the end user 100 from a generic template for avatar instantiation which is to be subsequently personalized to the end user 100 according to the characterization data 130. Specifically, once the avatar 170 has been instantiated according to the generic template, the characterization data 130 is transformed into a knowledge graph 140A. Specifically, the tokens of each phrase are both transformed into different records of a table indicating the textual terms and the part of speech relationship therebetween. Concurrently, the tokens are normalized into a uniform representation—namely a synset 140B including a set of synonyms produced by a synset engine.

Thereafter, once the knowledge graph 140A has been constructed for the end user 100 along with the synset 140B, a parameterization prompt 150 is constructed to include each of the knowledge graph 140A, synset 140B and also a textual directive to an LLM 160 to return a set of parameters 165 parameterizing the avatar 170 to specifically personalize the avatar 170 to the end user 100. Consequently, upon submitting the parameterization prompt 150 to the LLM 160, the LLM 160 returns the parameters 165 which in turn are applied to the avatar 170 in order to personalize the avatar 170 to the end user 100.

The avatar 170 is then submitted to a simulator 180 of the self-awareness computer program (not shown) in connection with a specific scenario document 175 describing a scenario soliciting a behavioral reaction by the avatar 170. The result is a prediction of the behavioral reaction within output data 185. For instance, the scenario document 175 can be a textual input such as a statement or a question. The simulator 180 receives the textual input and maps the input to a rule within the simulator taking as input, different parameters mapped to one or more data members of the avatar 170. The output of the rule is the output data 185 reflecting a prediction of the behavior of the end user 100 in light of the scenario within the scenario document 175.

A comparator then compares the output data 185 with model data 195 for the scenario document 175 in order to identify a discrepancy between a model behavior in response to the textual input and the actual behavior predicted by the avatar 170. The result of the comparison is placed in a deficiency artifact 190 which is then presented to the end user 100 in a user interface to the self-awareness program (not shown) in order to inform the end user 100 of a likely behavioral deficiency that can be corrected in advance of the scenario of the scenario document 175 coming to fruition.

Figure 2:
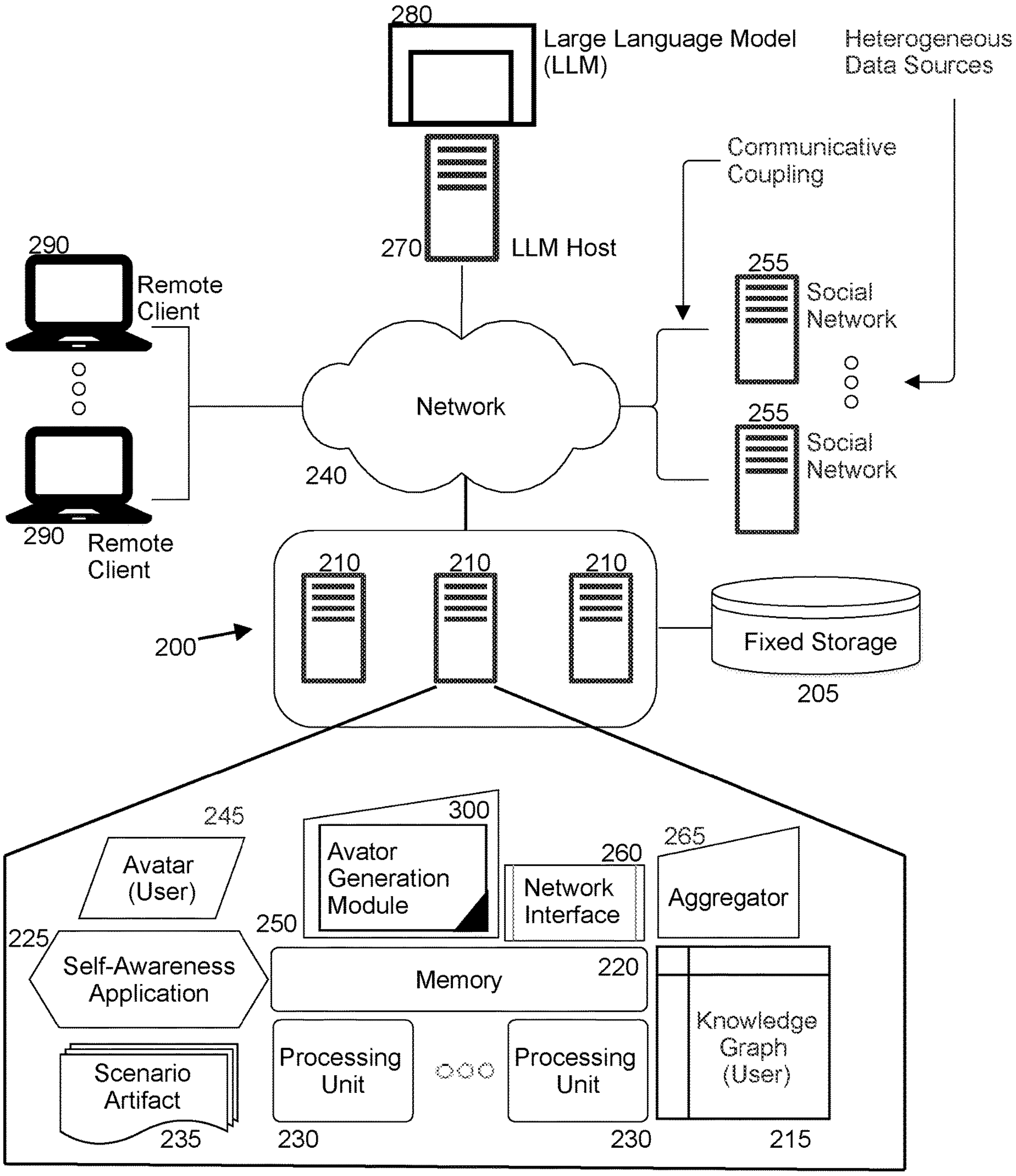
FIG. 2 is a block diagram depicting a data processing system adapted to perform one of the aspects of the process of FIG. 1; and, FIG. 3 is a flow chart illustrating one of the aspects of the process illustrated in FIG. 1.

Aspects of the process described in connection with FIG. 1 can be implemented within a data processing system. In further illustration, FIG. 2 schematically shows a data processing system adapted to perform virtual avatar generation and simulation. In the data processing system illustrated in FIG. 1, a host computing platform 200 is provided. The host computing platform 200 includes one or more computers 210, each with memory 220 and one or more processing units 230.

Fixed storage 205 also can be provided. The computers 210 of the host computing platform (only a single computer shown for the purpose of illustrative simplicity) can be co-located within one another and in communication with one another over a local area network, or over a data communications bus, or the computers can be remotely disposed from one another and in communication with one another through network interface 260 over a data communications network 240.

The host computing platform 200 is communicatively coupled over the computer communications network 240 to an LLM host 270 hosting access to an LLM 280. The host computing platform 200 further is communicatively coupled over the computer communications network 240 to one or more social networks 255 each supporting different social media content for different end users including postings and descriptive material. Finally, the host computing platform 200 is communicatively coupled to different remote clients 290 providing remote access to a self-awareness application 225 executing in the memory 220 by the one or more processing units 230 of the host computing platform 200.

Notably, a computing device 250 including a non-transitory computer readable storage medium can be included with the data processing system 200 and accessed by the processing units 230 of one or more of the computers 210 of the host computing platform 200. The computing device stores 250 thereon or retains therein a program module 300 that includes computer program instructions which when executed by one or more of the processing units 230, performs a programmatically executable process for virtual avatar generation and simulation. Specifically, the program instructions during execution register an end user interacting with the self-awareness platform 225 from a corresponding one of the remote clients 290 and invoke the aggregator 265 to collect characterization data of the end user, including without limitation from content accessible at the social networks 255. Thereafter, the program instructions direct the aggregator 265 to transform the characterization data into a knowledge graph 215 in the memory 220 along with a synset of the characterization data.

Of import, the program instructions instantiate an avatar 245 from a generic template and then personalize the avatar 245 for correspondence to the end user.

Specifically, the program instructions formulate an LLM prompt with the knowledge graph 215 and synset and a directive to produce a parameterization for the avatar 245.

Thereafter, the program instructions transmit the prompt over the data communications network 240 through the network interface 260 to the LLM Host 270. Upon receiving the parameterization from the LLM 280 by way of the LLM Host 270, the program instructions apply the parameterization to the avatar 245.

With the avatar 245 having been personalized to the end user, the program instructions then select a particular scenario 235 for simulation in the self-awareness application 225 and the program instructions simulate the particular scenario 235 against the personalized form of the avatar 245 in order to produce a predicted response by the avatar 245. The program instructions then compare the predicted response to a model response for the particular scenario 235 and produce an artifact recording differences between the predicted response and the model response. Finally, the program instructions display the artifact in the self-awareness application 225 to the end user.

Figure 3:
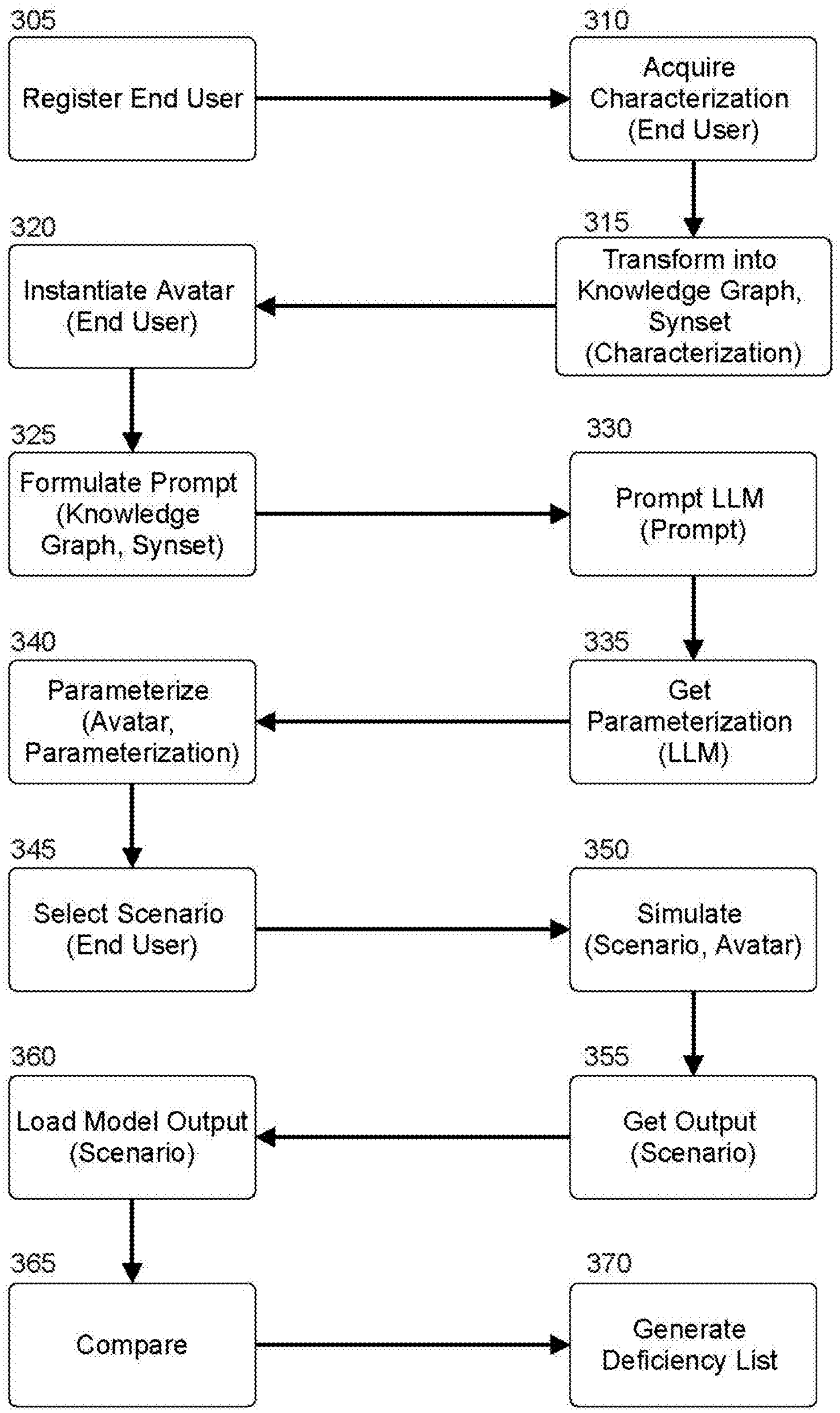

In further illustration of an exemplary operation of the module, FIG. 3 is a flow chart illustrating one of the aspects of the process of FIG. 1. Beginning in block 305, an end user registers with the self-awareness application. Thereafter, a characterization is acquired for the end user from a multiplicity of heterogeneous data sources, including responses to survey questions presented by the self-awareness application to the end user, content from real-time conversations between a bot of the self-awareness application and the end user and social media content accessible through an API to different social networks in connection with the end user.

In block 315, the acquired characterization data—namely textual tokens combined in different phrases of one or more tokens—is transformed concurrently into a knowledge graph and a synset, the knowledge graph including a triple store database table relating different ones of the tokens and the parts of speech linking those tokens, and the synset including different synonymous terms for each of the tokens. Then, in block 320 an avatar is instantiated according to a generic template and in block 325, an LLM prompt is formulated including the knowledge graph and synset. Subsequently, in block 330 the prompt is transmitted to an LLM with a directive to produce a parameterization of the avatar. In block 335, the parameterization is received from the LLM and in block 340 the avatar is parameterized using the parameterization generated by the LLM so as to personalize the avatar to the end user.

The personalized avatar is then simulated for a particular scenario in order to hypothesize how the end user would respond to the particular scenario. To do so, in block 345, the particular scenario is selected for simulation and in block 350, the simulation executes with the particular scenario and the avatar. For instance, the particular scenario can be one or more statements and the simulation can be one or more rules which are mapped to different ones of the statements and which take as input to the rules for evaluation, the data members of the avatar which personalize the avatar to the end user in order to produce a result of the rule. In block 355 the output from the evaluation of each of the rules of the simulation can be received from the simulator and in block 360 a model output for the evaluation of the rules of the particular scenario can be loaded. Subsequently, in block 365 the output from the evaluation is compared to the model output in order to generate a list of differences in an artifact 370 in order to express to the end user how to improve the behavior of the end user in order to cause an alignment with the model output.

Of import, the foregoing flowchart and block diagram referred to herein illustrate the architecture, functionality, and operation of possible implementations of systems, methods, and computing devices according to various embodiments of the present invention. In this regard, each block in the flowchart or block diagrams may represent a module, segment, or portion of instructions, which includes one or more executable instructions for implementing the specified logical function or functions. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

More specifically, the present invention may be embodied as a programmatically executable process. As well, the present invention may be embodied within a computing device upon which programmatic instructions are stored and from which the programmatic instructions are enabled to be loaded into memory of a data processing system and executed therefrom in order to perform the foregoing programmatically executable process. Even further, the present invention may be embodied within a data processing system adapted to load the programmatic instructions from a computing device and to then execute the programmatic instructions in order to perform the foregoing programmatically executable process.

To that end, the computing device is a non-transitory computer readable storage medium or media retaining therein or storing thereon computer readable program instructions. These instructions, when executed from memory by one or more processing units of a data processing system, cause the processing units to perform different programmatic processes exemplary of different aspects of the programmatically executable process. In this regard, the processing units each include an instruction execution device such as a central processing unit or "CPU" of a computer. One or more computers may be included within the data processing system. Of note, while the CPU can be a single core CPU, it will be understood that multiple CPU cores can operate within the CPU and in either instance, the instructions are directly loaded from memory into one or more of the cores of one or more of the CPUs for execution.

Aside from the direct loading of the instructions from memory for execution by one or more cores of a CPU or multiple CPUs, the computer readable program instructions described herein alternatively can be retrieved from over a computer communications network into the memory of a computer of the data processing system for execution therein. As well, only a portion of the program instructions may be retrieved into the memory from over the computer communications network, while other portions may be loaded from persistent storage of the computer. Even further, only a portion of the program instructions may execute by one or more processing cores of one or more CPUs of one of the computers of the data processing system, while other portions may cooperatively execute within a different computer of the data processing system that is either co-located with the computer or positioned remotely from the computer over the computer communications network with results of the computing by both computers shared therebetween.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Having thus described the invention of the present application in detail and by reference to embodiments thereof, it will be apparent that modifications and variations are possible without departing from the scope of the invention defined in the appended claims as follows:

We claim:

1. A method for virtual avatar generation and simulation comprising:

registering an end user in a self-awareness computer program;

establishing a communicative coupling to multiple different heterogeneous data sources and retrieving over each said coupling, characterizing data of the end user characterizing personality traits and demographic traits of the end user in a form of a multiplicity of tokens;

transforming the characterizing data into at least a portion of a knowledge graph in association with the end user by adding different records to a table indicative of textual terms of the multiplicity of the tokens and parts of speech therebetween and then normalizing the tokens into a synset;

instantiating an avatar according to a generic template in the self-awareness computer program in correspondence to the end user for subsequent personalization to the end user;

formulating an avatar generation prompt to a large language model (LLM) requesting a parameterization of the avatar and including both a reference to the knowledge graph and the synset, and also a reference to the avatar, transmitting the formulated prompt to the LLM and receiving the requested parameterization from the LLM in response to the transmitted avatar generation prompt;

parameterizing the avatar with the received parameterization; and, simulating the parameterized avatar in the self-awareness computer program with respect to a scenario artifact defining a scenario for the end user and soliciting a behavioral reaction by the avatar.

2. The method of claim 1, further comprising:

computing a performance of the parameterized avatar during the simulation;

comparing the computed performance to a benchmark value; and, recording a threshold disparity between the computed performance and the benchmark value in the self-awareness program in connection with the end user.

3. The method of claim 1, wherein the characterizing data includes answer data received from the end user in response to survey data presented to the end user in the self-awareness program.

4. The method of claim 1, wherein the characterizing data includes data extracted from natural language processing of free form communications by the end user and captured in the self-awareness program.

5. The method of claim 1, wherein the characterizing data includes demographic data extracted from a social media profile of the end user.

6. The method of claim 1, wherein the simulation comprises:

retrieving the scenario artifact from a repository of artifacts each describing a different action to be taken by the end user; and, applying a predictive rule to the different action with at least a portion of the avatar as an input parameter to the predictive rule; and, receiving a performance value in response to the application of the rule.

7. The method of claim 1, wherein the simulation comprises:

retrieving the scenario artifact from a repository of artifacts each describing a different action to be taken by the end user; and, formulating an avatar simulation prompt to the LLM requesting a performance value of the avatar in performing the action of the scenario artifact and including both a reference to the scenario artifact and also a reference to the avatar, transmitting the formulated avatar simulation prompt to the LLM and receiving the requested performance value in response to the transmitted avatar simulation prompt.

8. A data processing system adapted for virtual avatar generation and simulation, the system comprising:

a host computing platform comprising one or more computers, each with memory and one or processing units including one or more processing cores;

a self-awareness computer program executing in the host computing platform; and, an avatar generation module comprising computer program instructions enabled while executing in the memory of at least one of the processing units of the host computing platform to perform:

registering an end user in the self-awareness computer program;

establishing a communicative coupling to multiple different heterogeneous data sources and retrieving over each said coupling, characterizing data of the end user characterizing personality traits and demographic traits of the end user in a form of a multiplicity of tokens;

transforming the characterizing data into at least a portion of a knowledge graph in association with the end user by adding different records to a table indicative of textual terms of the multiplicity of the tokens and parts of speech therebetween and then normalizing the tokens into a synset;

instantiating an avatar according to a generic template in the self-awareness computer program in correspondence to the end user for subsequent personalization to the end user;

formulating an avatar generation prompt to a large language model (LLM) requesting a parameterization of the avatar and including both a reference to the knowledge graph and the synset, and also a reference to the avatar, transmitting the formulated prompt to the LLM and receiving the requested parameterization from the LLM in response to the transmitted avatar generation prompt;

parameterizing the avatar with the received parameterization; and, simulating the parameterized avatar in the self-awareness computer program with respect to a scenario artifact defining a scenario for the end user and soliciting a behavioral reaction by the avatar.

9. The system of claim 8, wherein the program instructions are further enabled to perform:

computing a performance of the parameterized avatar during the simulation;

comparing the computed performance to a benchmark value; and, recording a threshold disparity between the computed performance and the benchmark value in the self-awareness program in connection with the end user.

10. The system of claim 8, wherein the characterizing data includes answer data received from the end user in response to survey data presented to the end user in the self-awareness program.

11. The system of claim 8, wherein the characterizing data includes data extracted from natural language processing of free form communications by the end user and captured in the self-awareness program.

12. The system of claim 8, wherein the characterizing data includes demographic data extracted from a social media profile of the end user.

13. The system of claim 8, wherein the simulation comprises:

retrieving the scenario artifact from a repository of artifacts each describing a different action to be taken by the end user; and, applying a predictive rule to the different action with at least a portion of the avatar as an input parameter to the predictive rule; and, receiving a performance value in response to the application of the rule.

14. The system of claim 8, wherein the simulation comprises:

retrieving the scenario artifact from a repository of artifacts each describing a different action to be taken by the end user; and, formulating an avatar simulation prompt to the LLM requesting a performance value of the avatar in performing the action of the scenario artifact and including both a reference to the scenario artifact and also a reference to the avatar, transmitting the formulated avatar simulation prompt to the LLM and receiving the requested performance value in response to the transmitted avatar simulation prompt.

15. A computing device comprising a non-transitory computer readable storage medium having program instructions stored therein, the instructions being executable by at least one processing core of a processing unit to cause the processing unit to perform virtual avatar generation and simulation, by:

registering an end user in a self-awareness computer program;

establishing a communicative coupling to multiple different heterogeneous data sources and retrieving over each said coupling, characterizing data of the end user characterizing personality traits and demographic traits of the end user in a form of a multiplicity of tokens;

transforming the characterizing data into at least a portion of a knowledge graph in association with the end user by adding different records to a table indicative of textual terms of the multiplicity of the tokens and parts of speech therebetween and then normalizing the tokens into a synset;

instantiating an avatar according to a generic template in the self-awareness computer program in correspondence to the end user for subsequent personalization to the end user;

formulating an avatar generation prompt to a large language model (LLM) requesting a parameterization of the avatar and including both a reference to the knowledge graph and the synset, and also a reference to the avatar, transmitting the formulated prompt to the LLM and receiving the requested parameterization from the LLM in response to the transmitted avatar generation prompt;

parameterizing the avatar with the received parameterization; and, simulating the parameterized avatar in the self-awareness computer program with respect to a scenario artifact defining a scenario for the end user and soliciting a behavioral reaction by the avatar.

16. The device of claim 15, wherein the instructions are executable by at least one processing core of a processing unit to cause the processing unit to perform virtual avatar generation and simulation by further:

computing a performance of the parameterized avatar during the simulation;

comparing the computed performance to a benchmark value; and, recording a threshold disparity between the computed performance and the benchmark value in the self-awareness program in connection with the end user.

17. The device of claim 15, wherein the characterizing data includes answer data received from the end user in response to survey data presented to the end user in the self-awareness program.

18. The device of claim 15, wherein the characterizing data includes data extracted from natural language processing of free form communications by the end user and captured in the self-awareness program.

19. The device of claim 15, wherein the simulation comprises:

retrieving the scenario artifact from a repository of artifacts each describing a different action to be taken by the end user; and, applying a predictive rule to the different action with at least a portion of the avatar as an input parameter to the predictive rule; and, receiving a performance value in response to the application of the rule.

20. The device of claim 15, wherein the simulation comprises:

retrieving the scenario artifact from a repository of artifacts each describing a different action to be taken by the end user; and, formulating an avatar simulation prompt to the LLM requesting a performance value of the avatar in performing the action of the scenario artifact and including both a reference to the scenario artifact and also a reference to the avatar, transmitting the formulated avatar simulation prompt to the LLM and receiving the requested performance value in response to the transmitted avatar simulation prompt.

* * * * *